(12) United States Patent
Rama et al.

(10) Patent No.: US 9,090,537 B2
(45) Date of Patent: Jul. 28, 2015

(54) PROCESS FOR THE PREPARATION OF ALISKIREN

(71) Applicants: Shankar Rama, Hyderabad (IN); Seshadri Rao Manukonda, Hyderabad (IN); Srinivasa Rao Dasari, Hyderabad (IN); Ramesh Dandala, Hyderabad (IN); Lakshmana Rao Vadali, Hyderabad (IN)

(72) Inventors: Shankar Rama, Hyderabad (IN); Seshadri Rao Manukonda, Hyderabad (IN); Srinivasa Rao Dasari, Hyderabad (IN); Ramesh Dandala, Hyderabad (IN); Lakshmana Rao Vadali, Hyderabad (IN)

(73) Assignee: Mylan Laboratories Limited, Hyderabad (IN)

( * ) Notice: Subject to any disclaimer, the term of this patent is extended or adjusted under 35 U.S.C. 154(b) by 0 days.

(21) Appl. No.: 14/379,467

(22) PCT Filed: Feb. 15, 2013

(86) PCT No.: PCT/IN2013/000096
§ 371 (c)(1),
(2) Date: Aug. 18, 2014

(87) PCT Pub. No.: WO2013/121443
PCT Pub. Date: Aug. 22, 2013

(65) Prior Publication Data
US 2015/0011793 A1    Jan. 8, 2015

(30) Foreign Application Priority Data
Feb. 17, 2012  (IN) .............. 589/CHE/2012

(51) Int. Cl.
C07C 233/00   (2006.01)
C07C 231/12   (2006.01)
C07C 231/22   (2006.01)

(52) U.S. Cl.
CPC ............ *C07C 231/12* (2013.01); *C07C 231/22* (2013.01)

(58) Field of Classification Search
CPC .... C07C 231/12; C07C 231/22; C07C 233/11
USPC ..................................... 564/161, 191
See application file for complete search history.

(56) References Cited

U.S. PATENT DOCUMENTS

| 5,559,111 | A | 9/1996 | Göschke et al. |
| 6,730,798 | B2 | 5/2004 | Stutz et al. |
| 6,800,769 | B2 | 10/2004 | Stutz et al. |
| 7,009,078 | B1 | 3/2006 | Herold et al. |
| 7,132,569 | B2 * | 11/2006 | Herold et al. ................. 564/161 |

FOREIGN PATENT DOCUMENTS

WO    WO 2011/148392    12/2011

OTHER PUBLICATIONS

International Search Report for Int'l Application No. PCT/IN2013/000096, mailed Jul. 25, 2013.

* cited by examiner

*Primary Examiner* — Jafar Parsa

(57) ABSTRACT

The present invention relates to an improved process for the preparation of pure compound of Formula-II, which is an intermediate in the preparation of Aliskiren and further conversion of compound of Formula-II into Aliskiren or its pharmaceutically acceptable salts.

Formula-II

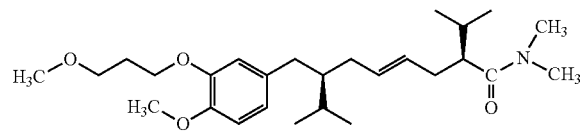

10 Claims, No Drawings

PROCESS FOR THE PREPARATION OF ALISKIREN

FIELD OF THE INVENTION

The present invention relates to an improved process for the preparation of renin inhibitor Aliskiren intermediates and further conversion into Aliskiren and its pharmaceutically acceptable salts.

BACKGROUND OF THE INVENTION

Aliskiren, (2S, 4S, 5S, 7S)-N-(2-carbamoyl-2-methylpropyl)-5-amino-4-hydroxy-2,7-diisopropyl-8-[4-methoxy-3-(3-methoxypropoxy)phenyl] octanamide having the Formula-I, a new antihypertensive has been developed which interferes with the renin-angiotensin system at the beginning of angiotensin II biosynthesis.

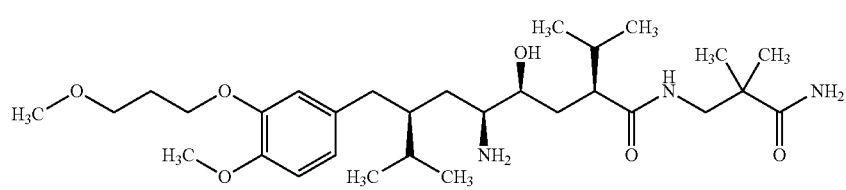

Formula-I

Aliskiren is marketed by Novartis as TEKTURNA® in the form of its hemifumarate salt in a once-daily formulation.

U.S. Pat. No. 5,559,111 discloses Aliskiren and related compounds along with the synthesis of Aliskiren.

Further U.S. Pat. No. 7,132,569, U.S. Pat. No. 7,009,078, U.S. Pat. No. 6,730,798 and U.S. Pat. No. 6,800,769 claims novel intermediates used in the preparation of Aliskiren and process for the preparation of Aliskiren, which are incorporated here for reference. U.S. Pat. No. 7,132,569 discloses compound of Formula-II, which is used as an intermediate in the preparation of Aliskiren and process for the preparation of the same.

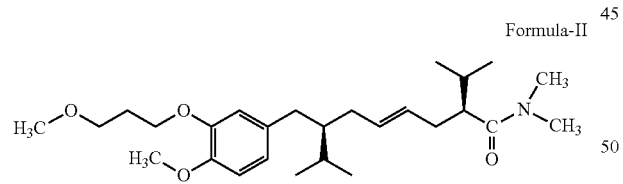

Formula-II

In this patent the obtained compound of Formula-II is purified by flash chromatography.

As the Aliskiren comprises, 4 chiral carbon atoms, the synthesis of the enantiomerically pure compound is quite demanding. The intermediate of Formula-II is commercially important in the synthesis of Aliskiren as well purity of the said intermediate play a vital role to achieve pure Aliskiren. Therefore an improved process for the said intermediate is needed to obtain pure intermediate which helps to obtain pure Aliskiren.

Thus the present invention provides an improved process for the preparation of Aliskiren intermediates and further conversion into Aliskiren.

OBJECT AND SUMMARY OF THE INVENTION

Principle object of the present invention is to provide an improved process for the preparation of intermediate of Formula-II of Aliskiren.

Another object of the present invention is to provide further conversion of intermediate of Formula-II into Aliskiren or its pharmaceutically acceptable salts.

One aspect of the present invention is to provide an improved process for the preparation of compound of Formula-II comprising

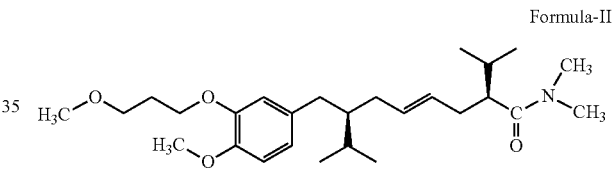

Formula-II condensing the compound of Formula-A with Compound of Formula-B, wherein the improvement comprises methylating the condensed crude product containing the mixture of compound of formula II and compound of Formula-C to get pure compound of Formula-II.

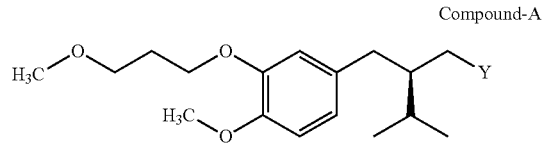

Compound-A

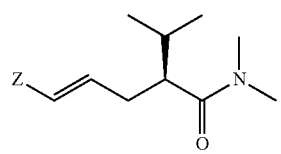

Compound-B

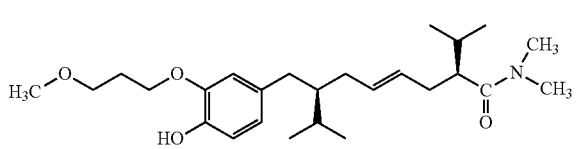

Formula-C wherein Y is Cl, Br or I, and Z is Cl, Br or I.

DETAILED DESCRIPTION OF THE INVENTION

The present invention relates to an improved process for the preparation of intermediate of Formula-II of Aliskiren.

The present invention also relates to conversion of compound of Formula-II into Aliskiren or its pharmaceutically acceptable salts.

The compound of Formula-II is prepared by condensing the compound of Formula-A with Compound of Formula-B as depicted in Scheme-I. When condensing the compound of Formula-A with Compound of Formula-B, hydroxy impurity of compound of Formula-C is formed at around 10-15%. The hydroxy compound is carry forward to the next stages of the process during the preparation of Aliskiren, which leads to lesser yields and impure Aliskiren. To avoid these problems present inventors surprisingly found that the compound of Formula-II is methylated after completion of the reaction.

In another embodiment, the obtained compound of Formula-II after methylation is purified by using fractional distillation method. First fraction is distilled out to remove impurity at a temperature of 130° C. to 200° C., (vapour temperature 40° C. to 130° C.), preferably at a temperature of 148° C. to 190° C., (vapour temperature 60° C. to 110° C.). Another fraction is distilled out at a temperature of 170° C. to 260° C., (vapour temperature 60° C. to 160° C.), preferably at a temperature of 198° C. to 240° C., (vapour temperature 80° C. to 140° C.). The remained residue is pure compound of Formula-II.

As per the present invention, the compound of Formula-A is reacted with alkali or alkaline earth metals like magnesium to yield corresponding Grignard reagent. The Grignard reagent is condensed with compound of formula B in an ether solvent such as, for example, tetrahydrofuran, methyl tetrahydrofuran or dioxan in the presence of catalytic quantities of a

SCHEME-I

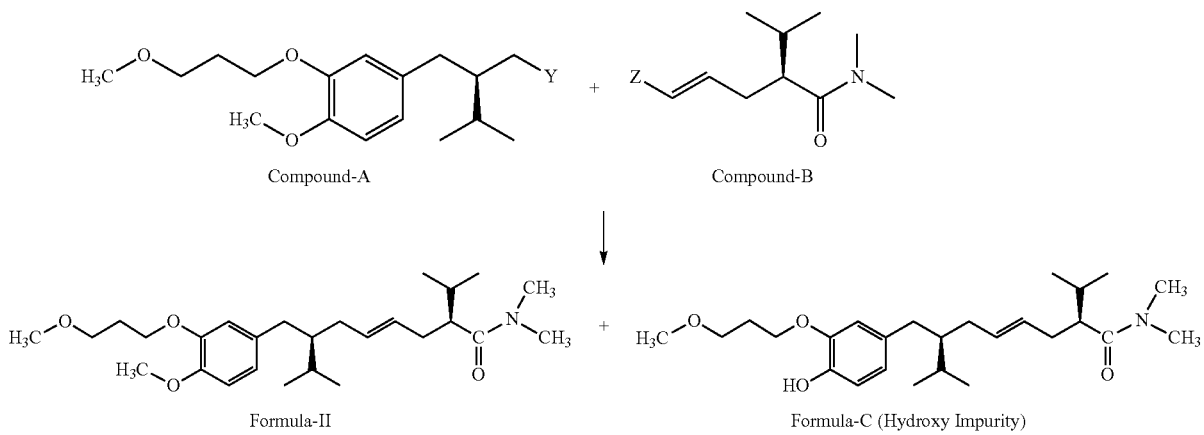

wherein Y is Cl, Br or I, and Z is Cl, Br or I.

Accordingly, main aspect of the present invention is to provide an improved process for the preparation of compound of Formula-II by condensing the compound of Formula-A with Compound of Formula-B in the presence of an alkali metal or alkaline earth metal, wherein the improvement comprises after completion of the reaction, the reaction mass containing the compound of formula II along with compound of Formula-C is methylated.

In one embodiment the methylation is carried out by using suitable methylating agent such as methyl iodide, dimethyl sulfate, Trimethylsulfoxonium iodide, preferably methyl iodide.

In one more embodiment, methylation is carried out optionally in presence of Phase transfer catalyst. The phase transfer catalyst used in this reaction is selected from tertramethyl ammonium bromide, tetrabutyl ammonium bromide, methyl triethyl ammonium bromide, benzyl trimethyl ammonium bromide, benzyl triethyl ammonium bromide, molecular sieves and crown ethers; preferably Tetra butyl ammonium bromide.

In another embodiment, the methylation is carried out in presence of base. The base used in this reaction is selected from alkali metal hydroxides or alkali metal hydroxides such as sodium hydroxide, potassium hydroxide, sodium methoxide, preferably sodium hydroxide.

In another embodiment, the methylation is carried out at 20-45° C., preferably at 25-35° C.

soluble metal complex, for example an iron complex such as iron acetonyl acetate, and in the presence of more than equimolar quantities of a solvent stabilizing the metal complex, for example N-methylpyrrolidone. After completion of the reaction the compound of formula-II is extracted with a suitable organic solvent like toluene from the reaction mass and to the organic layer and a base is added. Base is selected from alkali metal hydroxides such as sodium hydroxide, potassium hydroxide preferably sodium hydroxide; or alkali metal alkoxides such as sodium methoxide. Optionally a phase transfer catalyst like Tetra butyl ammonium bromide is added to the obtained reaction mass and stirred at room temperature. Then suitable methylation agent like methyl iodide is added dropwise and stirred at same temperature to yield pure compound of formula-II.

One more aspect of the present invention is to provide a compound of Formula-C, which is an impurity in the preparation of compound of Formula-II.

Formula-C

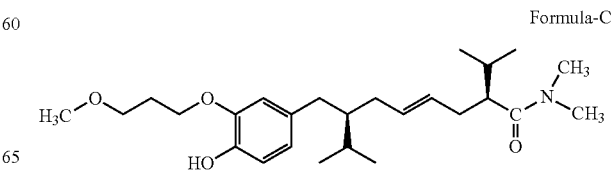

One more aspect of the present invention is to provide the compound of Formula-II having less than about 0.5% of compound of Formula-C (hydroxy impurity) at 0.92/0.93 RRT by HPLC.

cess into Aliskiren or its pharmaceutically acceptable salts by the conventional methods as described in U.S. Pat. No. 7,009,078 and the process disclosed in our co-pending Indian patent application IN 3087/CHE/2010 as depicted in the Scheme-II.

SCHEME-II

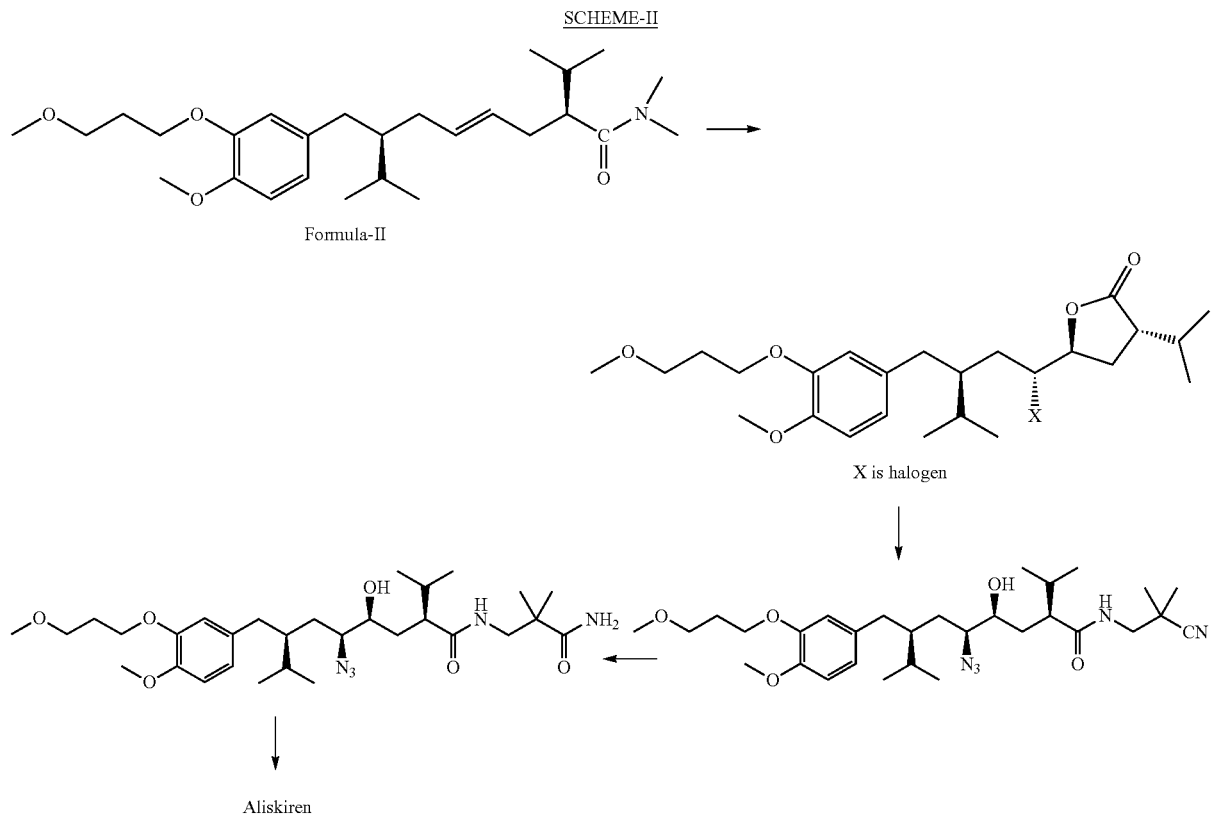

One more aspect of the present invention is to provide an improved process for the preparation of compound of Formula-II comprising methylating compound of Formula-C in presence of methylating agent.

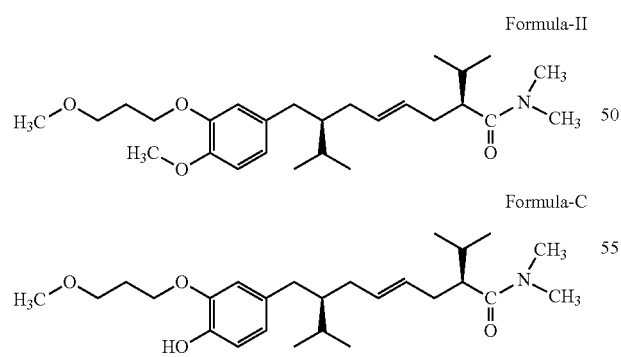

The compounds of Formula-A and Formula-B are prepared as per the conventional methods, for example the processes disclosed in U.S. Pat. No. 5,559,111 and U.S. Pat. No. 7,009,078.

Another aspect of the present invention is to provide further conversion of compound of Formula-II obtained by this pro- The following examples are provided to illustrate the process of the present invention. They, are however, not intended to limiting the scope of the present invention in any way and several variants of these examples would be evident to person ordinarily skilled in the art.

EXPERIMENTAL PROCEDURE

Example-1

Process for the Preparation of Compound of Formula-II (Where $R_1$=CH$_3$, R2=CH$_3$)

A mixture of Magnesium powder (14.1 g) and Tetrahydrofuran (175 ml) was heated to reflux and 1,2-dibromoethane (1 ml) was added over a period of 2 minutes. A solution of 2-{4-methoxy-3-(3-methoxypropoxyl)]-phenylmethyl-3-methyl-1-chlorobutane (100 g), 1,2-dibromoethane (3 g) and Tetrahydrofuran (350 ml) was added dropwise over a period of 90 minutes at 60-65° C. The reaction mixture was stirred under reflux and cooled to ambient temperature. There after this was added to a solution of 5-chloro-2-isopropyl-n,n-dimethylpent-4-enamide-(2S,4E) (27.5 g), N-methylpyrrolidone (0.80 g) and iron (III) acetyl acetonate (1.35 g) in Tetrahydrofuran (300 ml). The reaction mixture was agitated further 15 minutes at 10° C. and quenched with dilute hydrochloric acid. The reaction mixture was extracted with Toluene and the organic phases washed consecutively with water and saturated aqueous sodium chloride solution. To the combined toluene layer 2N Aq.sodium hydroxide solution (80 ml) was added at room temperature. Tetra butyl ammonium bromide (1 g) was added to the biphasic reaction and stirred at the same temperature for 15 minutes. Then 22 g of methyl iodide was added drop wise for 30 minutes and the resulting reaction mixture was stirred at the room temperature for further 10-12 hours. When the impurity at 0.92/0.93 rrt is less than 0.5% by HPLC, the reaction mass was diluted with water. The organic layer was separated, washed with water (1×100 ml), followed by brine washing (1×100 ml) and concentrated under vacuum to obtain the compound as a residue. The residue was subjected to high vacuum distillation to remove the volatile impurities (at ~225-235° C. temperature and at 0.1-1.0 mbar pressure) to obtain pure compound of Formula-II having the purity by HPLC 90-96%.

We claim:
1. An improved process for the preparation of compound of Formula-II comprising

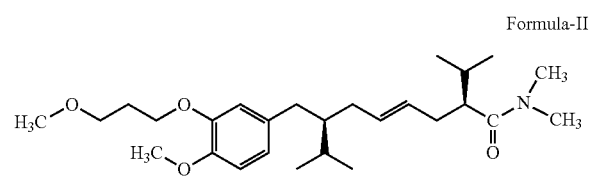
Formula-II condensing the compound of Formula-A with Compound of Formula-B, wherein the improvement comprises methylating the condensed crude product containing the mixture of compound of formula II and compound of Formula-C to get pure compound of Formula-II

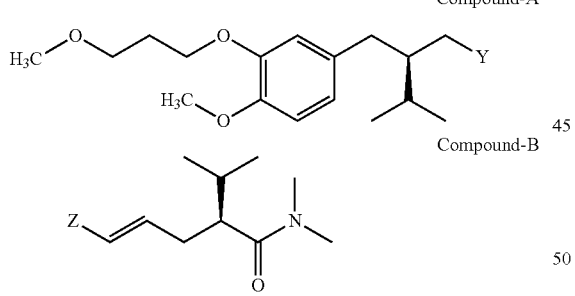
Compound-A

Compound-B

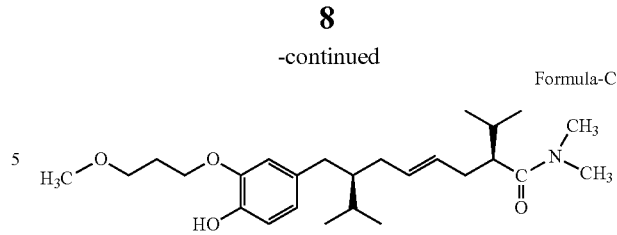
Formula-C wherein Y is Cl, Br or I, and Z is Cl, Br or I.

2. The process according to claim 1, wherein methylating agent is selected from methyl iodide or dimethyl sulfate.

3. The process of according to claim 1, where in methylation is carried out optionally in presence of phase transfer catalyst.

4. The process according to claim 3, wherein phase transfer catalyst is selected from tertramethyl ammonium bromide, tetrabutyl ammonium bromide, methyl triethyl ammonium bromide, benzyl trimethyl ammonium bromide, benzyl triethyl ammonium bromide, molecular sieves or crown ethers.

5. The process according to claim 1, wherein methylation is carried out in presence of base.

6. The process according to claim 5, wherein the base is selected from alkali metal hydroxides or alkali metal alkoxides.

7. The process according to claim 6, wherein the base is sodium hydroxide, potassium hydroxide or sodium methoxide.

8. The process according to claim 1, wherein compound of Formula-II is further converted into Aliskiren or it's pharmaceutically acceptable salts.

9. An improved process for the preparation of compound of Formula-II comprising methylating compound of Formula-C in presence of methylating agent.

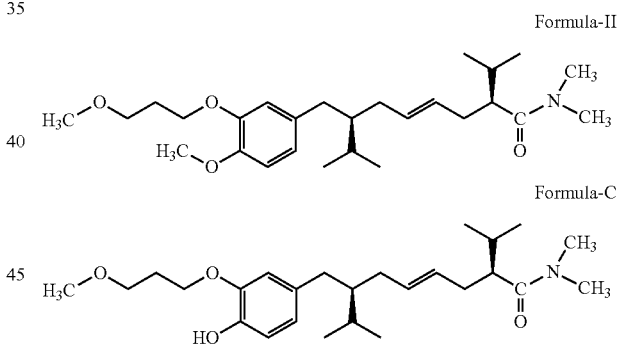

10. The process according to claim 9, wherein methylating agent is selected from methyl iodide or dimethyl sulfate.

* * * * *